United States Patent [19]

Horikawa

[11] Patent Number: 4,893,008

[45] Date of Patent: Jan. 9, 1990

[54] SCANNING OPTICAL MICROSCOPE

[75] Inventor: Yoshiaki Horikawa, Hachioji, Japan

[73] Assignee: Olympus Optical Co., Ltd., Tokyo, Japan

[21] Appl. No.: 204,277

[22] Filed: Jun. 9, 1988

[30] Foreign Application Priority Data

Jun. 9, 1987 [JP] Japan .................. 62-142218

[51] Int. Cl.⁴ .............................................. H01J 3/14
[52] U.S. Cl. ..................................... 250/234; 350/6.6
[58] Field of Search ....................... 250/201, 234, 235; 356/444; 350/6.6, 6.91

[56] References Cited

U.S. PATENT DOCUMENTS 4,745,270 5/1988 Horikawa et al. .................. 250/234
4,800,269 1/1989 Horikawa ............................ 250/234

Primary Examiner—Edward P. Westin
Assistant Examiner—Khaled Shami
Attorney, Agent, or Firm—Kenyon & Kenyon

[57] ABSTRACT

A scanning optical microscope comprises a light source, an objective lens for focusing light emitted from the light source upon an object to be observed, a light deflecting optical system provided between the light source and the objective lens and including a light deflector formed by an acousto-optic light deflector (AOD), photoelectric transducing means for detecting light from the object, and light shielding means having an elongated aperture provided between the object and the photoelectric transducing means. Light from the light source is deflected by the AOD to scan the object at a high speed, and light from the object is led to the photoelectric transducing means through the aperture of the light shielding means, without passing through the AOD, to realize confocal microscopy.

11 Claims, 5 Drawing Sheets

SCANNING OPTICAL MICROSCOPE

BACKGROUND OF THE INVENTION

1. Field of the Invention

This invention relates to a scanning optical microscope, and more particularly to a scanning optical microscope having a confocal optical system by which an object can be scanned at a high speed.

2. Description of the Prior Art

In a scanning optical microscope, light from a light source such as a laser is focused as a minute light spot on an object by an objective lens, and the object is scanned by the light spot to obtain an image of the object. Compared with conventional optical microscopes, scanning optical microscopes provide images of high contrast since no diffused light comes from the area other than the light spot. Further, special microscopy such as confocal microscopy, differential phase microscopy, etc., can be done easily by scanning optical microscopes, and it is also possible to visualize various physical phenomena which cannot be observed by means of conventional optical microscopes, such as OBIC (optical beam induced current) images, photo-acoustic images, etc. Therefore, scanning optical microscopes are expected to be useful microscopes in the semiconductor and material industries as well as biology and medical science.

Many of the conventional scanning optical microscopes scan an object by moving in a horizontal direction a stage on which the object is mounted, without shifting the position of a light spot, or by providing a reflecting mirror such as a polygonal rotating mirror, a galvanometer mirror, etc., in the optical path from a light source to an objective lens to shift in a horizontal direction a light spot formed on an object. However, since these scanning systems cannot come up with the horizontal scanning of a television system because of their low scanning speed, real-time observation of an object is impossible. In order to resolve such problem, the inventor of the present invention has proposed in a laid-open Japanese patent application, publication No. 61-219919, a scanning optical microscope in which an acousto-optic light deflector (hereinafter AOD, if applicable) is used instead of the above-mentioned mirror so that the scanning speed can be higher and real-time observation of an object can be made.

FIG. 1 shows an optical system of a scanning optical microscope disclosed in the laid-open Japanese patent application, publication No. 61-219919. The optical system comprises a beam splitter 1, a first light deflector 2 formed by an AOD, pupil transfer lenses 3 and 4, a second light deflector 5, a pupil projection lens 6, an imaging lens 7, and an objective lens 8. Numeral 9 denotes a pupil of the objective lens 8 and numeral 10 denotes an object or specimen. The second light deflector 5 is arranged in the position conjugate with the pupil 9 of the objective 8 with respect to the pupil projection lens 6 and the imaging lens 7, and the first light deflector 2 is located in the position conjugate with the second light deflector 5 with respect to the pupil transfer lenses 3 and 4. The first light deflector 2 performs horizontal scanning while the second light deflector 5 effectuates vertical scanning. Further, a collector lens 11, a pinhole 12 and a detector 13 are arranged.

A beam 14 from a light source (not shown) such as a laser passes through the beam splitter 1 and enters the first light deflector 2. The light exiting from the first light deflector 2 varies in its exit angle from the most deflected position shown by the dotted lines through the non-deflected position shown by the full lines to the most deflected position on the opposite side (not shown). The beam 14 passes through the pupil transfer lenses 3 and 4 and enters the second light deflector 5 where the exit angle of light varies in the same manner as in the first light deflector 2. The beam 14 deflected two-dimensionally by both light deflectors 2 and 5 is caused to enter the pupil 9 of the objective 8 by the pupil projection lens 6 and the imaging lens 7. Further, the beam 14 is focused to its diffraction limit and scans the specimen 10 two-dimensionally. The light reflected from the specimen 10 returns through the objective 8, the imaging lens 7, the pupil projection lens 6, the second light deflector 5, the pupil transfer lenses 4 and 3, and the first light deflector 2. The returned reflected light is taken out by the beam splitter 1 and becomes a detection beam 17. Since the detection beam 17 has passed the light deflectors 5 and 2 again, it returns to the same position. The detection beam 17 is focused by the collector lens 11 and detected by the detector 13 through the pinhole 12. Thus, an image of high resolution by reflected light can be obtained.

In addition to high resolution of an image, this method using a pinhole has an important feature that a sliced image of an object can be obtained as described below.

FIG. 2 illustrates a principle of obtaining a sliced image of an object by reflected light when a pinhole is used, that is, the principle of confocal microscopy. For the purpose of simplification, the scanning optical system is omitted. There are shown a point light source 21, a beam splitter 22, an objective lens 23, a specimen 24, a pinhole 25, and a detector 26. The pinhole 25 is located in a position conjugate with the point light source 21, that is, an image of the point light source 21 is formed on a plane 27 in the specimen 24 by the objective 23, and the image is formed again at the pinhole 25 by the same objective 23. Therefore, the above-described system is called a confocal system.

Light from the point light source 21 enters the objective 23 and illuminates a point in the plane 27 in the specimen 24. Reflected light becomes a beam 29 which is reflected by the beam splitter 22, passes through the pinhole 25 and is detected by a detector 26. A light beam 30 reflected from another plane 28 (located out of focus) in the specimen 24 has an expansion at the pinhole 25 and therefore hardly reaches the detector 26. Thus, since light other than that from the plane 27 including the point illuminated by the point light source 21 is not detected, a sliced image of a thick specimen can be easily obtained.

In reality, a light scanning system as shown in FIG. 1 is inserted between the point light source 21 and the objective lens 23. Since the pinhole 25 is minute and cannot be moved in synchronism with scanning, the pinhole 25 must be positioned on the same side as the light source 21 with respect to the light scanning system.

In the above, confocal microscopy by using light reflected from an object is described. However, if the same scanning optical microscope is used for confocal fluorescence microscopy, the following problems arise:

An AOD is a device for deflecting light through diffraction grating produced by a sound wave. The deflection angle $\theta$, i.e., the angle between a light beam incident on an AOD and a light beam exiting from the AOD is given by the following formula:

$$\theta = f \frac{\lambda}{v}$$

where
λ is the wavelength of the light incident on the AOD;
v is the sound velocity in the AOD; and
f is the frequency of a sound wave applied to the AOD. Therefore, the deflection angles $\theta_L$ and $\theta_F$ of a laser beam of wavelength $\lambda_L$ projected on an object and a fluorescent beam of wavelength $\lambda_F$ emitted from the object, respectively are given by the following formulas:

$$\theta_L = f \frac{\lambda_L}{v}, \theta_F = f \frac{\lambda_F}{v}.$$

Thus, even if the same sound wave is applied to the same AOD, the deflection angles differ from each other. Consequently, when an AOD intervenes, traveling directions of a laser beam and a fluorescent beam are different from each other, so that both beams do not come to the same position. Therefore, the pinhole 12 in FIG. 1 must be shifted slightly in a direction perpendicular to the optical axis, depending upon which is used for observing an object, a laser beam or a fluorescent beam. Moreover, the difference between the deflection angles of a laser beam and a fluorescent beam, represented by the following formula:

$$\Delta\theta = \theta_L - \theta_F = \frac{f}{v}(\lambda_L - \lambda_F)$$

varies with the frequency f of a sound wave. Thus, when the deflection angle is varied by varying the value f in order to scan an object, the amount of discrepancy between the traveling directions of the laser beam and the fluorescent beam varies. Strictly speaking, unless the position of the pinhole 12 in FIG. 1 is minutely adjusted in accordance with the variation of the deflection angle, fluorescent light of wavelength $\lambda_F$ goes out of the pinhole 12 (instead, fluorescent light having a slightly different wavelength passes through the pinhole 12), so that an accurate fluorescence microscopy cannot be realized.

Moreover, the diffraction efficiency of an AOD is dependent on the wavelength of incident light. When an AOD having a high diffraction efficiency for laser beams is used, there is a problem that the diffraction efficiency for fluorescent beams is low and the intensity of fluorescent light is reduced.

As described above, in a scanning optical microscope disclosed in the laid-open Japanese patent application, publication No. 61-219919, the detection of a sliced image of a specimen by using fluorescent light can be realized in principle by a detection method using a pinhole. However, since the detection is performed through an AOD, the wavelength of detected fluorescent light varies and the diffraction efficiency cannot be improved. Thus, this scanning optical microscope is not practical.

SUMMARY OF THE INVENTION

An object of the present invention is to provide a scanning optical microscope which allows a high-speed scanning by using an AOD and a practical confocal microscopy by using fluorescent light.

In order to achieve the above object, a scanning optical microscope according to the present invention is provided with an AOD in the optical path between a light source and an object to be observed so that the object can be scanned at a high speed. Light from the object is led to a photoelectric transducing means without passing through the AOD so that it is possible to eliminate the drawbacks arising from the variation of the deflection angle of fluorescent light and the reduction of diffraction efficiency in the AOD. In this case, the light incident on the photoelectric transducing means moves in an amplitude corresponding to the deflection by the AOD. However, since there is provided, instead of a pinhole, an elongated aperture (slit) along the direction of deflection of the incident light, the light is not blocked and confocal microscopy can be effectuated.

This and other objects as well as the features and the advantages of the present invention will be apparent from the following detailed description of the preferred embodiments when taken in connection with the accompanying drawings.

DETAILED DESCRIPTION OF THE PREFERRED EMBODIMENTS

Figure 3:
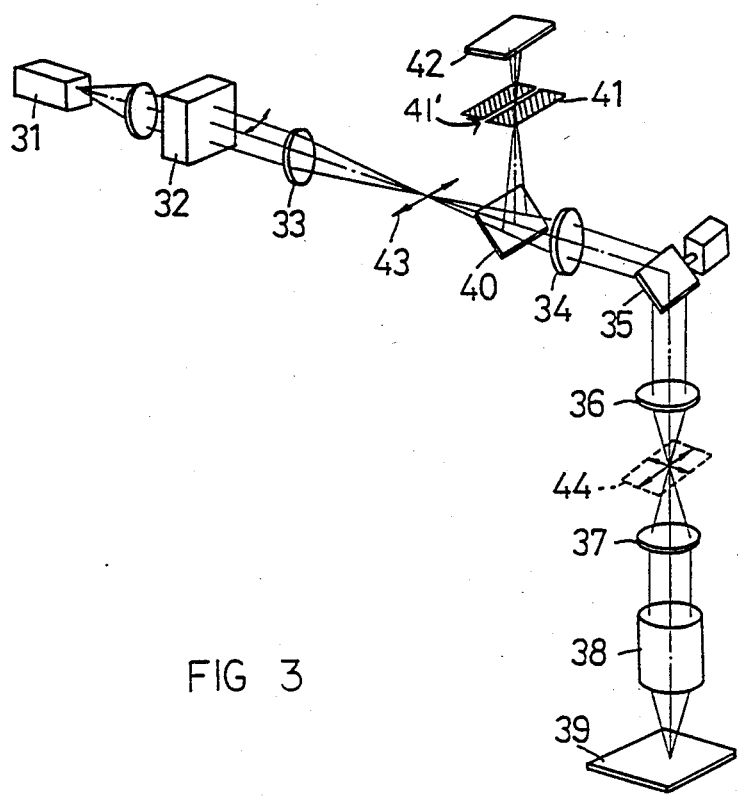
FIG. 3 is a perspective view showing an embodiment of an optical system for a scanning optical microscope according to the present invention.

FIG. 3 shows an embodiment of the present invention which includes in the following order a laser beam source 31, an AOD 32 for horizontal scanning, pupil transfer lenses 33 and 34, a galvanometer mirror 35 for vertical scanning, a pupil projection lens 36, an imaging lens 37, and an objective lens 38. Numeral 39 denotes a specimen. The AOD 32 and the galvanometer mirror 35 are located in the pupil position. A beam splitter 40 is arranged between the pupil transfer lenses 33 and 34. Over the beam splitter 40, there are provided an opaque plate 41 having an elongated aperture (slit) 41' in a direction parallel to the direction of horizontal scanning, and a detector 42.

Light from the laser beam source 31 enters the AOD 32 and undergoes to horizontal deflection. Then, the light passes through the pupil transfer lenses 33 and 34, impinges on the galvanometer mirror 35 and undergoes vertical deflection. The light spot deflected by the AOD 32 constitutes one-dimensional scanning 43. The light spot deflected by the galvanometer mirror 35 passes through the pupil projection lens 36 and constitutes two-dimensional scanning 44 in the image plane of the imaging lens 37. Finally, the light spot passes through the objective 38 and scans the specimen 39 two-dimensionally. Reflected light or fluorescent light from the specimen 39 returns to the galvanometer mirror 35 through the objective lens 38, etc., and is taken out from the optical scanning system by the beam splitter 40. The light so taken out moves one-dimensionally in the same manner as the light spot at the position 43, and passes through the slit 41' to be detected by the detector 42.

The above-described structure makes it possible to observe an specimen in real time by performing horizontal scanning at a high speed with an AOD and vertical scanning with a galvanometer mirror. Further, since reflected light or fluorescent light is detected before it re-enters the AOD, drawbacks of prior art, such as the variation of the wavelength of detected fluorescent light and the impossibility of improving the diffraction efficiency, are eliminated. Moreover, since light to be detected is refocused and detected through a slit, confocal microscopy can be performed to obtain a sliced image of a thick specimen.

The width of the elongated aperture of the opaque plate 41 may be smaller or larger than the diffraction diameter of spot light. If it is smaller, the resolution in the direction of depth of focus (thickness of the specimen) can be theoretically small. The larger the width is, the more information on planes other than the focal plane may be obtained.

In the above, a reflection type of two-dimensional scanning system has been described. In the case of a transmission type, an optical system is provided to return the light transmitted through an object to the other light deflecting member which is not an acousto-optic light deflector, and the light passing the light deflecting member is received through a slit so that confocal microscopy can be realized similarly.

Figure 4:
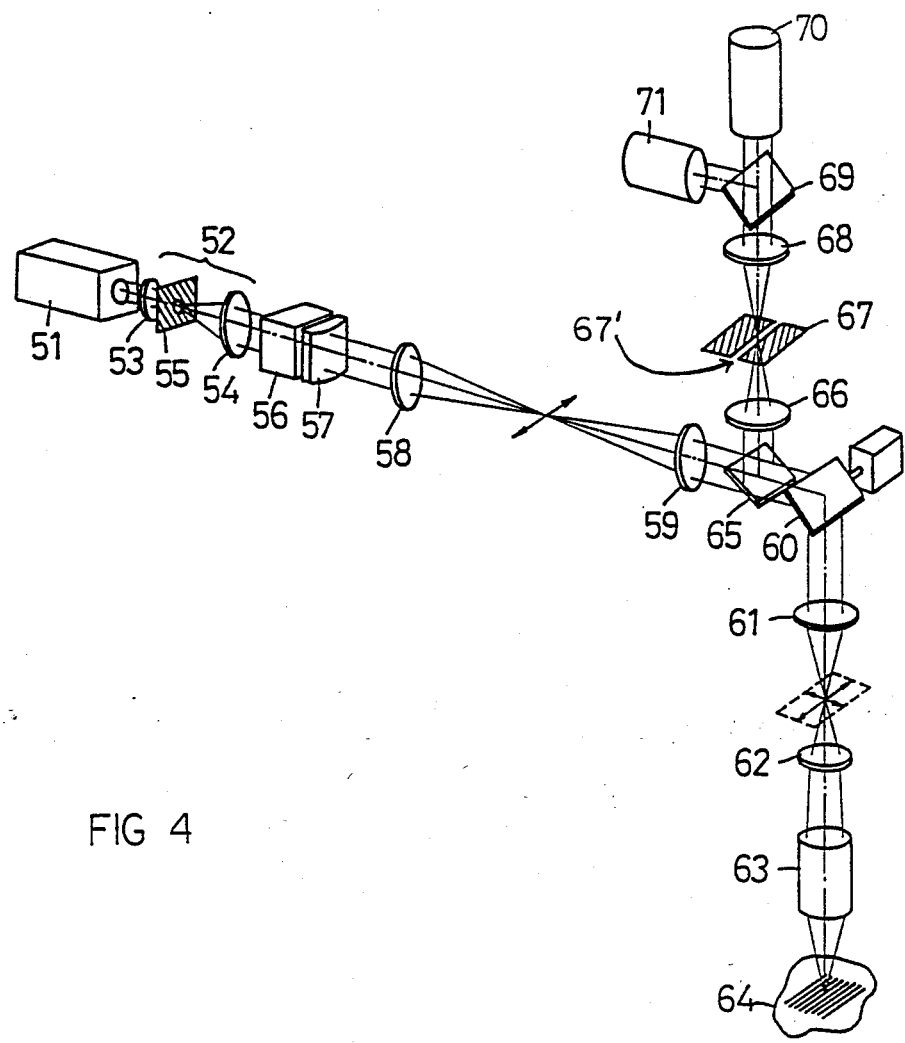
FIG. 4 is a perspective view showing another embodiment of an optical system for a scanning optical microscope according to the present invention.

FIG. 4 shows another embodiment which includes in the following order a laser beam source 51 for fluorescence excitation, such as Ar+ laser and He-Cd-laser; a beam expander 52 including two lenses 53 and 54 and a pinhole 55 arranged between the lenses 53 and 54 to serve as a spatial filter; an AOD 56 for performing deflection with the frequency of 15.75 KHz corresponding to the horizontal scanning of the NTSC television system; and a cylindrical lens 57 for correcting the lens effect on an outgoing beam caused by a high-speed deflection of the AOD 56. In front of the cylindrical lens 57, pupil transfer lenses 58 and 59 are arranged in such a manner that the AOD 56 exists in the pupil position, that is, the AOD 56 is in an optically conjugate relationship with a galvanometer mirror 60. The galvanometer mirror 60 is also arranged in the pupil position and performs deflection with the frequency of 60 Hz corresponding to the vertical scanning of the NTSC television system. The deflection by the AOD 56 and the galvanometer mirror 60 causes 60 times per second of two-dimensional scanning. Under the galvanometer mirror 60, there are provided a pupil projection lens 61, an imaging lens 62 and an objective lens 63. Numeral 64 denotes a specimen. A beam splitter 65 is positioned between the pupil transfer lens 59 and the galvanometer mirror 60. Over the beam splitter 65, a collector lens 66 is arranged. An opaque plate 67 is located in the focusing position of the collector lens 66 and having an elongated aperture (slit) 67' parallel to the direction of horizontal scanning. Over the slit 67', there are provided a pupil projection lens 68, dichroic mirror 69 for splitting light into reflected light for excitation and fluorescent light, and detectors 70 and 71, one of which detects reflected light and the other detects fluorescent light. The pupil projection lens 68 is to project the pupil image on the light receiving surfaces of the detectors 70 and 71 so that the beam is fixed on the detectors 70 and 71. The opaque plate 67 is located in a positions conjugate with the pinhole 55 and the specimen 64. In order to detect fluorescent light, it is preferable that the detectors 70 and 71 are photomultiplier tubes.

Now, the operation of this embodiment is described. A laser beam emitted from the beam source 51 is expanded by the beam expander 52 to have a proper beam diameter and enters the AOD 56 to be deflected for horizontal scanning, and the outgoing beam is corrected by the cylindrical lens 57. After passing through the pupil transfer lenses 58 and 59, the laser beam is deflected for vertical scanning by the galvanometer mirror 60 to constitute a two-dimensional scanning state, passes through the pupil projection lens 61, the imaging lens 62 and the objective 63 and is focused to a minute spot which scans the specimen 64 two-dimensionally.

Light reflected from the specimen 64 and fluorescent light pass again through the objective 63, the imaging lens 62 and the pupil projection lens 61 and returns to the galvanometer mirror 60. After the reflected light and fluorescent light are reflected by the galvanometer mirror 60 with vertical scanning eliminated, the same splitter 65 takes out the light to be detected. After passing through the slit 67' and the pupil projection lens 68, the light to be detected is split by the dichroic mirror 69 into the reflected light and fluorescent light which are detected by the detectors 70 and 71. Video signals obtained by the detectors 70 and 71 are displayed in synchronism with the scanning. Since the light is detected through the slit 67', a sliced image is obtained. Thus, when a stage with the specimen 64 mounted thereon is moved up and down, the specimen 64 can be observed three-dimensionally.

As described above, it is possible to realize real-time observation of sliced images of a thick specimen obtained by reflected light and fluorescent light. Since a thick specimen can be observed in real time, a living biological specimen can be observed and thus this embodiment is suitable for observing minute structure of DNA, etc. Moreover, since the returning light is detected after it is retransformed into one-dimensional scanning light and before it re-enters the AOD, this embodiment is free from the drawbacks such that the wavelength of detected light varies or that the diffraction efficiency cannot be improved, thus, it is practical.

Figure 5:
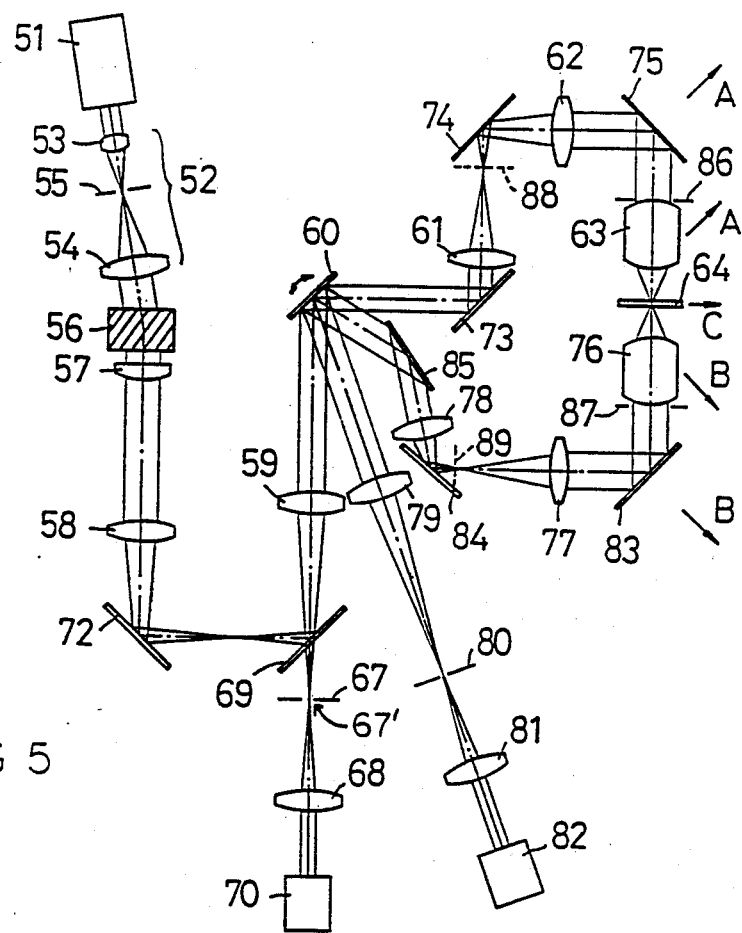
FIG. 5 is a schematic view showing still another embodiment of an optical system for a scanning optical microscope according to the present invention.

FIG. 5 shows still another embodiment which permits the observation of sliced images of a specimen obtained by fluorescent light and transmitted light. The same elements as those in the second embodiment are assigned the same numerals and their description is omitted. This embodiment includes mirrors 72, 73, 74 and 75 for merely deflecting the optical path. A dichroic mirror 69 is designed to reflect 100% of light for excitation of short wavelength and transmit 100% of fluorescent light of long wavelength. An AOD 56 is illustrated in such a manner that the AOD 56 is inclined and deflects light in the plane of the drawing sheet, but in reality it is inclined and deflects light in a plane perpendicular to the drawing sheet.

This embodiment also includes pairs of objective lenses 63 and 76, imaging lenses 62 and 77, pupil projection lenses 61 and 78, pupil transfer lenses 59 and 79, slits 67 and 80, pupil projection lenses 68 and 81, and detectors 70 and 82 for observing fluorescent light and reflected light, respectively. Mirrors 83, 84 and 85 are also provided only to deflect the optical path. It is so designed that the magnification of the image of the pupil 86 of the objective 63 projected on a galvanometer mirror 60 by the optical system including the pupil projection lens 61 is identical to the magnification of the image of the pupil 87 of the objective lens 76 projected on the galvanometer mirror 60 by the optical system including the pupil projection lens 78.

In this embodiment so constructed, a laser beam emitted from the light source 51 is expanded by the beam expander 52 to have a proper beam diameter and enters the AOD 56 to be deflected for horizontal scanning, and the outgoing beam is corrected by the cylindrical lens 57. After passing through the pupil transfer lens 58, the beam is reflected by the mirror 72 and the dichroic mirror 69, passes through the pupil transfer lens 59 and is deflected for vertical scanning by the galvanometer mirror 60 to constitute a two-dimensional scanning state. Then, the beam is focused on the image plane 88 of the objective 63 via the mirror 73 and the pupil projection lens 61, enters the pupil 86 of the objective 63 via the mirror 74, the imaging lens 62 and the mirror 75 and is focused by the objective 63 to a minute spot which scans the specimen 64 two-dimensionally.

Fluorescent light emitted from the specimen 64 passes through the objective 63, the imaging lens 62 and the pupil projection lens 61 and returns to the galvanometer mirror 60. After it is reflected by the galvanometer mirror 60 with vertical scanning eliminated, the fluorescent light passes through the pupil projection lens 59 and the dichroic mirror 69 and is focused on the opaque plate 67. After passing through the slit 67′ positioned in the focusing position and the pupil projection lens 68, the light is detected by the detector 70. Video signals obtained by the detector 70 from the fluorescent light are displayed in synchronism with the scanning. Since the light is detected through the slit 67′, a sliced image is obtained. Thus, when a stage with the specimen 64 mounted thereon is moved up and down, a three-dimensional observation by fluorescence is possible.

On the other hand, the laser beam transmitted through the specimen 64 is focused on the image plane 89 of the objective 76 via the objective 76, the mirror 83 and the imaging lens 77 and impinges upon the galvanometer mirror 60 via the mirror 84 and the pupil projection lens 78. After it is reflected from the galvanometer mirror 60 to be retransformed into a one-dimensional scanning state, the laser beam enters the pupil transfer lens 79 and passes through the slit 80 and the pupil projection lens 81 to be detected by the detector 82.

In this case, as described above, it is so designed that the magnification of the image of the pupil 86 of the objective 63 projected on the galvanometer mirror 60 by the optical system including the pupil projection lens 61 is identical to the magnification of the image of the pupil 87 of the objective 76 projected on the galvanometer mirror 60 by the optical system including the pupil projection lens 78. Therefore, the transmitted light having returned through the optical system including the pupil projection lens 78, too, can be retransformed to be in a complete one-dimensional scanning state by the galvanometer mirror 60. Thus, since a confocal optical system is formed by the slit 80, too, a sliced image by transmitted light can be obtained. Further, if the specimen 64 is moved in the direction of the optical axis, three-dimensional observation is possible.

Figure 1:
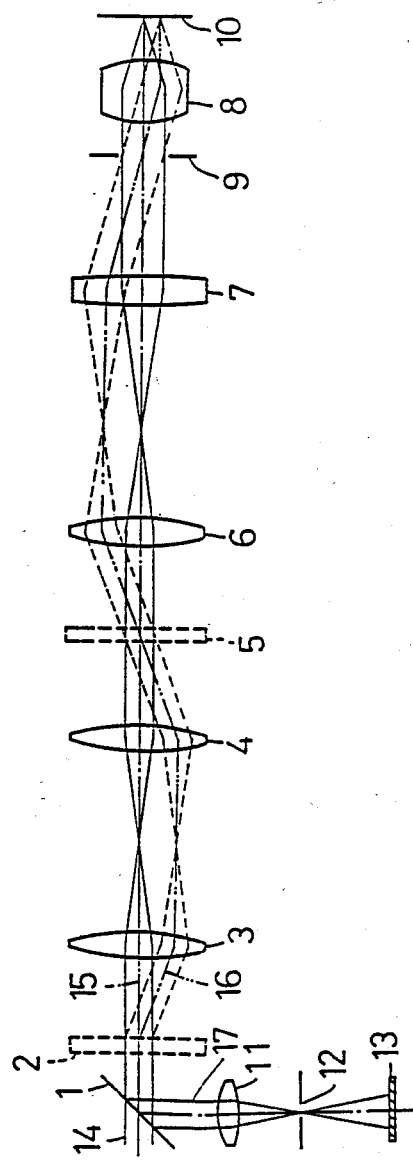
FIG. 1 is a schematic view of a conventional optical system for a scanning optical microscope.
Figure 6:
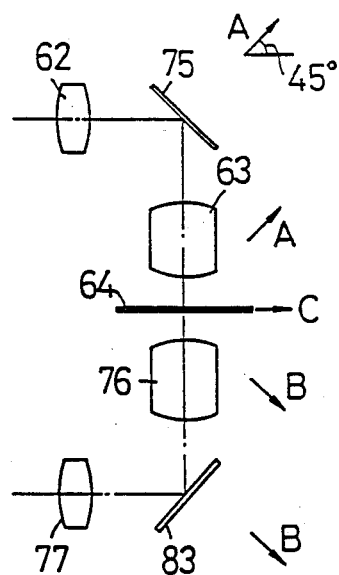
FIG. 6 is a schematic view showing a principle of keeping constant the length of the light path between the objective lenses in the embodiment shown in FIG. 5.
Figure 2:
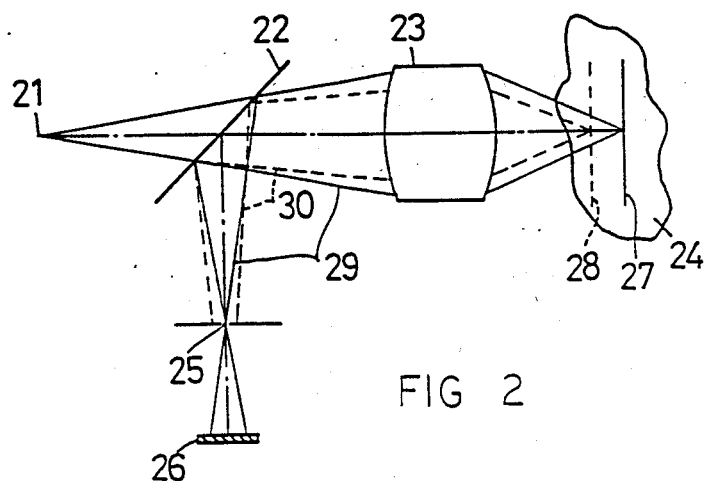
FIG. 2 is a schematic view showing a principle of confocal microscopy.

In this connection, it should be noted that the length of optical path through the specimen 64 varies with each specimen. In order to keep the optical system for transmitted light being always in the confocal state, it is necessary to adjust the distance between the objectives 63 and 76 in accordance with the length of optical path through the specimen 64 to keep constant the length of optical path between the objectives 63 and 76 irrespective of what kind of specimen is observed. However, if the objectives 63 and 76 only are moved up and down, the image planes 88 and 89 of the objectives 63 and 76 will shift accordingly, so that no confocal system can be maintained. In order to solve this problem, adjustment of the optical system as shown in FIG. 6 is proposed. That is, the mirror 75 and the objective 63 are shifted in the direction indicated by the arror A inclined to the optical axis by 45°, and the objective lens 76 and the mirror 83 are moved in the direction indicated by the arrow B inclined to the optical axis by 45°. With this structure, the adjustment of distance between the objectives 63 and 76 does not cause the shift of the image planes 88 and 89, so that the confocal optical system can be maintained. In this case, the objectives 63 and 76 also shift slightly in a horizontal direction. If the specimen 64 is also moved in the direction indicated by the arrow C without changing its relative position with respect to the objectives 63 and 76, it is possible to hold the specimen 64 always in the same position in the field of view. Needless to say, the mirrors 75 and 83, the objectives 63 and 76, and the specimen 64 are sifted by a mechanism for moving them systematically, not separately.

Thus, this embodiment allows the observation of sliced images obtained by fluorescent light and transmitted light, which is of practical use. Further, in the case of detection by transmitted light, the light transmitted through a specimen is returned to the same light deflector (galvanometer mirror 60) that deflects the incoming light, so that it is not necessary to synchronize different light deflectors and therefore a confocal optical system can be realized by a simple optical system.

As described above, a scanning optical microscope according to the present invention has an important advantage that sliced images obtained by reflected light, transmitted light and fluorescent light can be observed practically.

What is claimed is:

1. A scanning optical microscope comprising:
   a light source;
   an objective lens for focusing light emitted from said light source upon an object to form a minute light spot on said object;
   a light deflecting optical system arranged between said light source and said objective lens and including at least one acousto-optic light deflector for varying the angle of incidence on said objective lens of the light emitted from said light source so as to scan said object with said light spot;
   light splitting means provided in said light deflecting optical system and between said acousto-optic light deflector and said objective lens for taking out at least a part of the light coming from said object;
   focusing means for focusing the light taken out by said light splitting means;
   light shielding means arranged in the focusing position of said focusing means and having an elongated aperture, the longitudinal direction of said elongated aperture being coincident with the direction of movement of the light in said focusing position; and photoelectric transducing means for receiving the light passing through said aperture of said light shielding means.

2. A scanning optical microscope according to claim 1 further comprising a light deflector formed by movable reflecting means provided in said light deflecting optical system and between said light splitting means and said objective lens for varying the angle of incidence on said objective lens of the light emitted from said light source, said reflecting means being so arranged as to vary the angle of incidence in a direction perpendicular to the direction of variation of the angle of incidence caused by said acousto-optic light deflector, so that said object is scanned two-dimensionally by said light spot.

3. A scanning optical microscope according to claim 2 wherein said reflecting means is provided in a position optically conjugate with the pupil of said objective lens, and said acousto-optic light deflector is provided in a position optically conjugate with said reflecting means.

4. A scanning optical microscope according to claim 3 wherein said photoelectric transducing means is provided in a position optically conjugate with said reflecting means.

5. A scanning optical microscope according to claim 3 further comprising optical path splitting means provided in the path of light passing through said aperture of said light shielding means for transmitting light having a first wavelength and reflecting light having a second wavelength different from said first wavelength, said photoelectric transducing means including first and second photoelectric transducing means for receiving separately the light transmitted and reflected by said optical path splitting means.

6. A scanning optical microscope according to claim 3 further comprising object supporting means for supporting said object, said object supporting means being movable in a direction along the optical axis of said objective lens.

7. A scanning optical microscope according to claim 5 wherein said light having a first wave length is the light emitted from said light source and reflected from said object, and said light having a second wave length is fluorescent light emitted from said object due to said object having been illuminated by the light emitted from said light source.

8. A scanning optical microscope comprising:
a light source;
an objective lens for focusing light emitted from said light source upon an object to form a minute light spot on said object;
a light deflecting optical system arranged between said light source and said objective lens and including at least one acousto-optic deflector and a light deflector for varying the angle of incidence on said objective lens of the light emitted from said light source so as to scan said object with said light spot, said latter light deflector being formed by movable reflecting means;
a relay optical system for leading light from said object to said light deflector formed by said movable reflecting means;
focusing means for focusing the light which impinges on said light deflector through said relay optical system and is reflected from said light deflector;
light shielding means arranged in the focusing position of said focusing means and having an elongated aperture, the longitudinal direction of said elongated aperture being coincident with the direction of movement of the light in said focusing position; and
photoelectric transducing means for receiving the light passing through said aperture of said light shielding means.

9. A scanning optical microscope according to claim 8 wherein said light deflector and said acousto-optic light deflector are arranged in optically conjugate relationship with each other, and one of said light deflector and said acousto-optic light deflector is provided in a position optically conjugate with the pupil of said objective lens.

10. A scanning optical microscope according to claim 9 wherein said relay optical system includes a second objective lens having the same structure that said objective lens has, and said light deflector and the pupil of said second objective lens are arranged in optically conjugate relationship with each other.

11. A scanning optical microscope according to claim 10 wherein object supporting means for supporting said object is provided, said object supporting means being movable in a direction perpendicular to the optical axis of said objective lens, and said objective lens and said second objective lens are so arranged as to be movable in oblique upper and lower directions, respectively, with respect to a plane perpendicular to the optical axis of said objective lens, while the points of intersection of the optical axes of said objective lens and said second objective lens with said object are fixed.

* * * * *